(12) United States Patent
Gliner

(10) Patent No.: US 6,263,240 B1
(45) Date of Patent: Jul. 17, 2001

(54) ELECTROTHERAPY METHOD

(75) Inventor: Bradford E Gliner, Issaquah, WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/687,833

(22) Filed: Oct. 13, 2000

Related U.S. Application Data

(62) Division of application No. 09/283,705, filed on Apr. 1, 1999.

(51) Int. Cl.$^7$ ..................................................... A61N 1/39
(52) U.S. Cl. ............................................................ 607/5
(58) Field of Search ........................... 607/5, 8; 600/515, 600/518

(56) References Cited

U.S. PATENT DOCUMENTS

| | | | |
|---|---|---|---|
| 4,202,340 | * | 5/1980 | Langer et al. .................... 128/419 |
| 5,620,465 | * | 4/1997 | Olson et al. ........................ 607/5 |
| 5,632,766 | * | 5/1997 | Hsu et al. .......................... 607/5 |

* cited by examiner

Primary Examiner—William E. Kamm

(57) ABSTRACT

An electrotherapy apparatus, such as a defibrillator, includes a connecting mechanism coupled between an energy source and electrodes. The connecting mechanism allows selective coupling of the energy source to the electrodes. The energy source includes a capacitor and a high voltage power supply for charging the capacitor. The electrotherapy apparatus further includes a waveform measuring device for measuring a patient ECG waveform. The electrotherapy apparatus also includes a controller coupled to the connecting mechanism, the energy source, and the waveform measuring device. The controller actuates the connecting mechanism to deliver a bi-phasic waveform to the patient. In addition, the controller analyzes the ECG waveform to detect when the patient is experiencing either course arrhythmia or fine arrhythmia. The detection of course arrhythmia or fine arrhythmia can be done by comparing the amplitude of the ECG waveform to a predetermined amplitude value, by comparing the power spectrum of the ECG waveform to a predetermined frequency value, by measuring the duration of the arrhythmia, or by measuring some combination of these ECG waveform characteristics. Based upon whether the patient is experiencing course arrhythmia or fine arrhythmia, the controller adjusts the amplitude and/or duration of the bi-phasic waveform applied to the patient to optimize the likelihood of defibrillation.

9 Claims, 3 Drawing Sheets

ELECTROTHERAPY METHOD

CROSS REFERENCE TO RELATED APPLICATION

This is a divisional of copending application Ser. No. 09/283,705 filed on Apr. 1, 1999.

FIELD OF THE INVENTION

This invention relates to electrotherapy, and more particularly to a method and apparatus for applying electrotherapy.

BACKGROUND OF THE INVENTION

Heart arrhythmia, such as ventricular fibrillation (VF), can be classified based upon the characteristics of the ECG waveform measured during arrhythmia. in general, the characteristics of the ECG waveform measured during arrhythmia change as the episode progresses. The changes in the characteristics of the ECG waveform indicate that there is likely an underlying physical change in the heart associated with the progression of the arrhythmia. Because of changes in the heart resulting from the progression of arrhythmia, there is a need for an electrotherapy method and apparatus that adjusts the electrotherapy applied to the patient based upon changes in the characteristics of arrhythmia.

SUMMARY OF THE INVENTION

Accordingly, an electrotherapy apparatus and a method for performing electrotherapy on a patient have been developed to meet this need. A method for performing electrotherapy on the patient includes measuring patient related information. The method further includes determining a characteristic of an arrhythmia using the patient related information. The method additionally includes supplying an electrotherapy waveform to the patient having a property based upon the characteristic of the arrhythmia.

An electrotherapy apparatus for performing electrotherapy on a patient through a first electrode and a second electrode includes an energy source to provide energy for performing electrotherapy. The electrotherapy apparatus also includes a connecting mechanism configured for coupling and decoupling the energy source to and from, respectively, the first electrode and the second electrode. The electrotherapy apparatus further includes a measuring device for measuring patient related information. Additionally, the electrotherapy apparatus includes a controller coupled to the connecting mechanism and the energy source and arranged to receive the patient related information from the measuring device. The controller includes a configuration for determining a characteristic of an arrhythmia from the patient related information. The controller also includes a configuration for adjusting the energy delivered to the patient based upon the characteristic of the heart arrhythmia.

A defibrillator for delivering a multi-phasic waveform to a patient through a first electrode and a second electrode includes a capacitor having a first terminal and having a second terminal. The capacitor is used to store charge for delivery of the multi-phasic waveform to the patient. The defibrillator further includes a power supply configured for charging the capacitor. The defibrillator also includes a connecting mechanism coupled between the first terminal and the second terminal of the capacitor and the first electrode and the second electrode to permit the first terminal of the capacitor to selectively couple to one of the first electrode and the second electrode and to permit the second terminal of the capacitor to selectively couple to one of the first electrode and the second electrode. The defibrillator further includes a waveform measuring device for measuring an ECG waveform. Additionally, the defibrillator includes a controller coupled to the connecting mechanism and arranged to receive the ECG waveform from the waveform measuring device. The controller includes a configuration to adjust the multi-phasic waveform based upon the ECG waveform.

DESCRIPTION OF THE DRAWINGS

A more thorough understanding of the invention may be had from the consideration of the following detailed description taken in conjunction with the accompanying drawings in which.

DETAILED DESCRIPTION OF THE DRAWINGS

The present invention is not limited to the specific exemplary embodiments illustrated in this specification. Although the electrotherapy apparatus will be discussed in the context of operation external to a patient, it should be recognized that the disclosed principles are adaptable to an electrotherapy apparatus which operates internal to the patient. Furthermore, although the operation of the electrotherapy apparatus will be discussed in the context of a patient experiencing arrhythmia such as ventricular fibrillation, it should be recognized that the principles disclosed also apply to a patient experiencing other forms of arrhythmia such as ventricular tachycardia. In addition, although the electrotherapy apparatus will be discussed in the context of the application of a bi-phasic electrotherapy waveform, it should be recognized that the disclosed principles are adaptable to an electrotherapy apparatus which applies other types of electrotherapy waveforms, such as mono-phasic, multi-phasic, or damped sinusoid waveforms.

Figure 1:
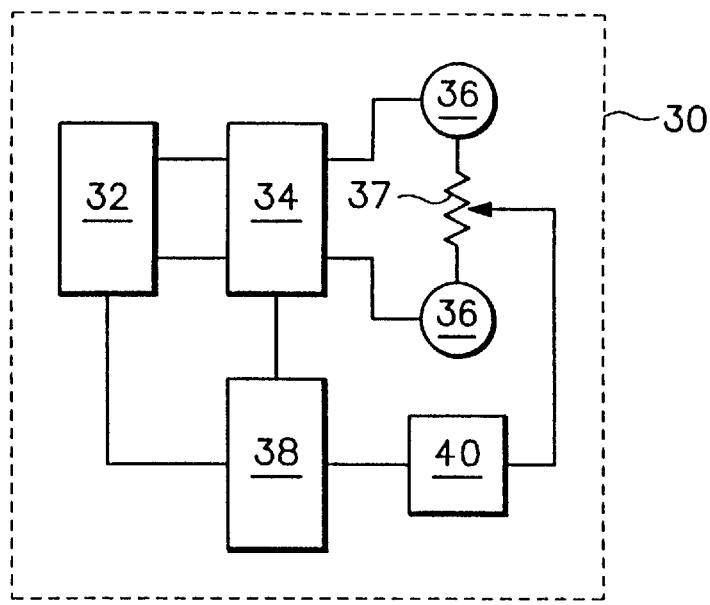
FIG. 1 shows a high level block diagram of an electrotherapy apparatus.

Shown in FIG. 1 is a high level block diagram of an electrotherapy apparatus 30, such as a defibrillator, that includes the ability to adjust the electrotherapy applied to the patient based upon the characteristic of the arrhythmia experienced by the patient. The electrotherapy apparatus 30 includes an energy source 32 to provide the energy for an electrotherapy waveform. Energy source 32 may include, for example, a single capacitor or a capacitor bank arranged to act as a single capacitor. A connecting mechanism 34 selectively connects and disconnects energy source 32 to and from a pair of electrodes 36 electrically attached to a patient, with the patient represented here as a resistive load 37. The connections between the electrodes and the energy source may be in either of two polarities with respect to positive and negative terminals on the energy source. The electrotherapy apparatus 30 is controlled by a controller 38. Specifically, controller 38 operates the connecting mechanism 34 to connect energy source 32 with electrodes 36 in one of the two polarities or to disconnect energy source 32 from electrodes 36.

Controller 38 is coupled to energy source 32 to configure the energy source 32 in preparation for delivering the energy for the electrotherapy waveform. Configuring the energy source 32 may include, for example, setting a voltage on a capacitor included in energy source 32. Measuring device 40 measures patient related information and provides this patient related information to controller 38. Measuring device 40 could include a waveform measuring device for performing a measurement related to the arrhythmia of the heart (for example, to generate an electrical representation of patient heart activity, such as an ECG waveform). Measuring device 40 could alternatively include a sensor for providing a measurement related to the exhalation of carbon dioxide, such as an $ETCO_2$ measurement, or a measurement related to the oxygen content of the patient's blood, such as an $SaO_2$ measurement. FIG. 1 schematically depicts the coupling between measuring device 40 and the patient (represented by resistive load 37) that would occur for various embodiments of measuring device 40 (such as an waveform measuring device, or a carbon dioxide sensor, or an oxygen sensor).

For the case in which measuring device 40 includes a waveform measuring device, measuring device 40 would be electrically coupled to the patient. The electrical coupling could be through electrodes 36 or through separate electrodes attached to the patient that are not used to apply the electrotherapy waveform. For the case in which the measuring device includes a sensor for providing an $ETCO_2$ measurement, this measurement could be collected from a sensor placed in the patient's throat. For the case in which the measuring device includes a sensor for providing a $SaO_2$ measurement, this measurement could be collected from a sensor placed in the patient's blood stream.

Controller 38 is coupled to measuring device 40 and configured to receive the patient related information generated by measuring device 40. The analysis of the patient related information by controller 38 provides an indication of the healthiness of the patient's heart. For the case in which the patient related information includes an ECG waveform, controller 38 could perform operations, under the control of firmware, on the ECG waveform to determine a characteristic of the arrhythmia. The analysis of the ECG waveform performed by controller 38 could include determining whether the patient is experiencing either course arrhythmia or fine arrhythmia.

Controller 38 could control energy source 32 and/or connecting mechanism 34 to supply an electrotherapy waveform to the patient having a property based upon the characteristics of the arrhythmia. For example, the property of the electrotherapy waveform could include the shape of the electrotherapy waveform. Controller 38 could control the coupling and decoupling of energy source 32 to electrode 36 using the connecting mechanism 34 in order to control the shape of the electrotherapy waveform applied to the patient. Or, controller 38 could configure energy source 32 by, for example, setting a voltage on a capacitor included in the energy source 32, in order to control the shape of the electrotherapy waveform applied to the patient. Or, controller 38 could control both the coupling and decoupling of the energy source to electrodes 36 and the voltage on the capacitor in the energy source 32 in order to control the shape of the electrotherapy waveform applied to the patient.

Figure 2:
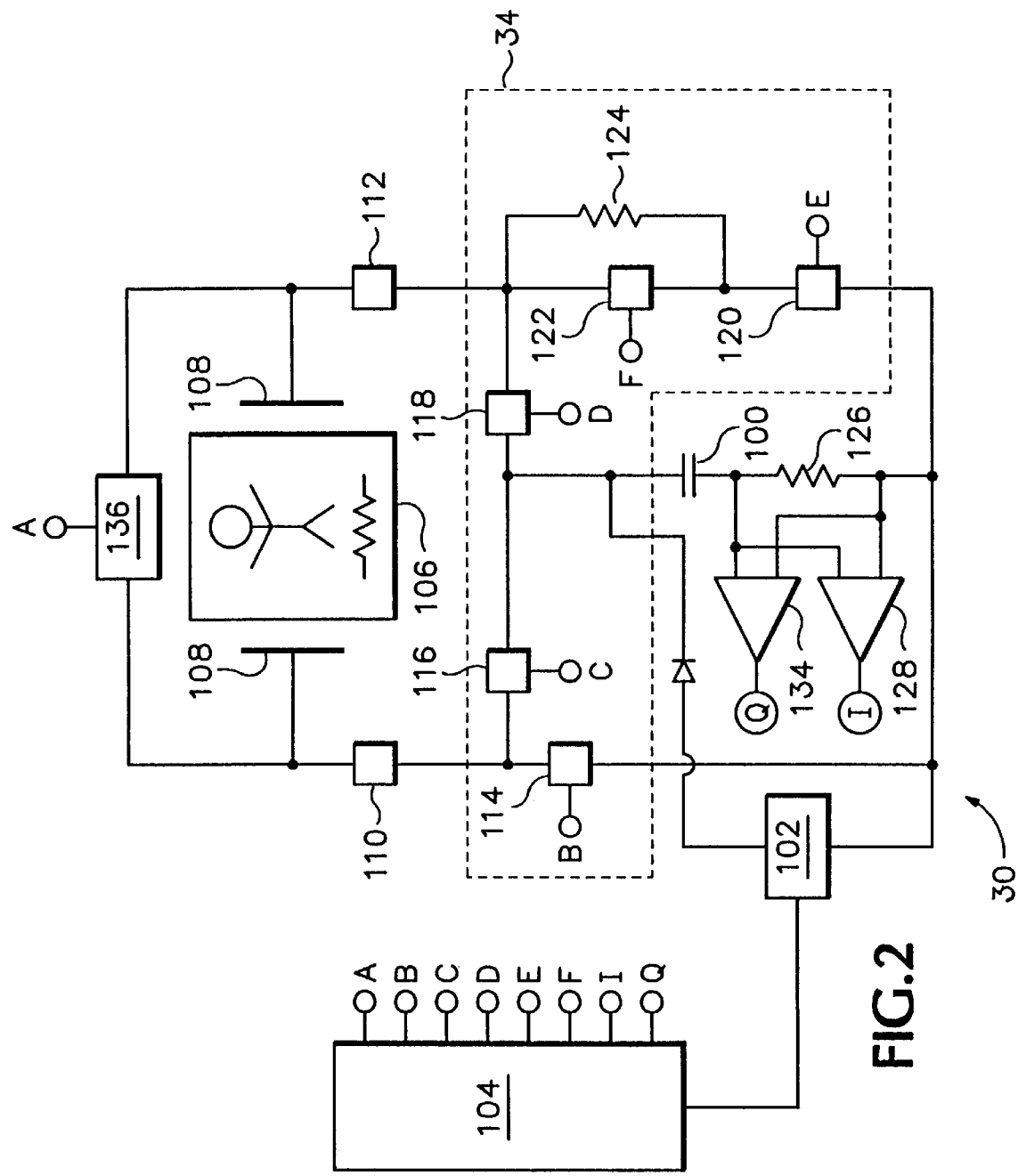
FIG. 2 shows a simplified schematic of an embodiment of the electrotherapy apparatus shown in FIG. 1.

Shown in FIG. 2 is a simplified schematic showing an embodiment of electrotherapy apparatus 30 represented by the block diagram shown in FIG. 1. In FIG. 2, the energy source includes a capacitor 100 having a capacitance value between 60 and 150 microfarads, with an optimal capacitance value of 100 microfarads. The electrotherapy apparatus 30 also includes a charging device, such as high voltage power supply 102, for charging the capacitor 100 to an initial voltage. A controller 104 controls the operation of the electrotherapy apparatus to automatically deliver an electrotherapy waveform to the patient (represented by patient impedance 106) through electrodes 108 in response to a detected arrhythmia or manually in response to a human operator.

Switches 110 and 112 isolate the patient from the defibrillation circuitry until the application of the bi-phasic electrotherapy waveform. Switches 110 and 112 may be any suitable kind of isolators, such as mechanical relays, solid state devices, spark gaps, or other gas discharge devices. In this embodiment of the electrotherapy apparatus, the connecting mechanism 34 includes four switches 114, 116, 118, and 120 operated by the controller 104 to deliver an electrotherapy waveform from capacitor 100 to the patient. Switch 122 is connected in parallel across resistor 124 to control the peak current flowing into the patient impedance 106. A current monitor measures the flow of current provided by capacitor 100 to patient impedance 106. The current monitor includes a sense resistor 126 through which the current from capacitor 100 flows. An amplifier 128 amplifies the voltage that appears across sense resistor 126. The voltage across sense resistor 126 is proportional to the current flowing from capacitor 100. The output of amplifier 128 is connected to controller 104. Controller 104 includes an output coupled to switch 122. Current integrator 134 provides charge information to the controller 104 that could be used to measure the energy delivered to the patient.

Waveform measuring device 136 provides an ECG waveform to controller 104. Controller 104 performs an analysis of the data in the ECG waveform in order to determine whether an electrotherapy waveform should be applied to the patient to stop arrhythmia. If controller 104 determines that electrotherapy is required, controller 104 then initiates the process necessary for delivering the electrotherapy waveform to patient impedance 106.

At the end of the first phase of the electrotherapy waveform, the controller opens switch 120 to terminate delivery of the electrotherapy waveform. The controller 104 opens switch 116 as well. After the lapse of a brief interphase period, the controller closes switches 114 and 118 to initiate delivery of the second phase of the electrotherapy waveform. At the end of the second phase, the controller 104 opens switch 114 to terminate delivery of the shock. Switches 118, 110, and 112 are opened after the opening of switch 114.

Amplifier 128 can be used to send a signal proportional to the current flow through resistor 126 to the controller 104. Amplifier 128 may be implemented using an operational amplifier configured as a differential amplifier. Current integrator 134 may be implemented using an op-amp feeding a threshold comparator for detecting charge limits. The current integrator 134 could include a switch for resetting to its initial conditions prior to the initiation of an electrotherapy waveform.

In addition to determining whether electrotherapy should be applied to the patient based upon the ECG waveform, controller 104 includes the capability to adjust a property of the electrotherapy waveform applied to the patient based upon the ECG waveform. Controller 104 analyzes the ECG waveform to determine the optimal electrotherapy waveform shape to apply to the patient. Based upon this analysis of the ECG waveform and in order to achieve the optimally shaped electrotherapy waveform, controller 104 may adjust, for example, the initial voltage to which capacitor 100 should be charged or the duration of the electrotherapy waveform applied to the patient, in order to improve the likelihood of defibrillation into a beneficial post-shock heart rhythm.

Figure 3:
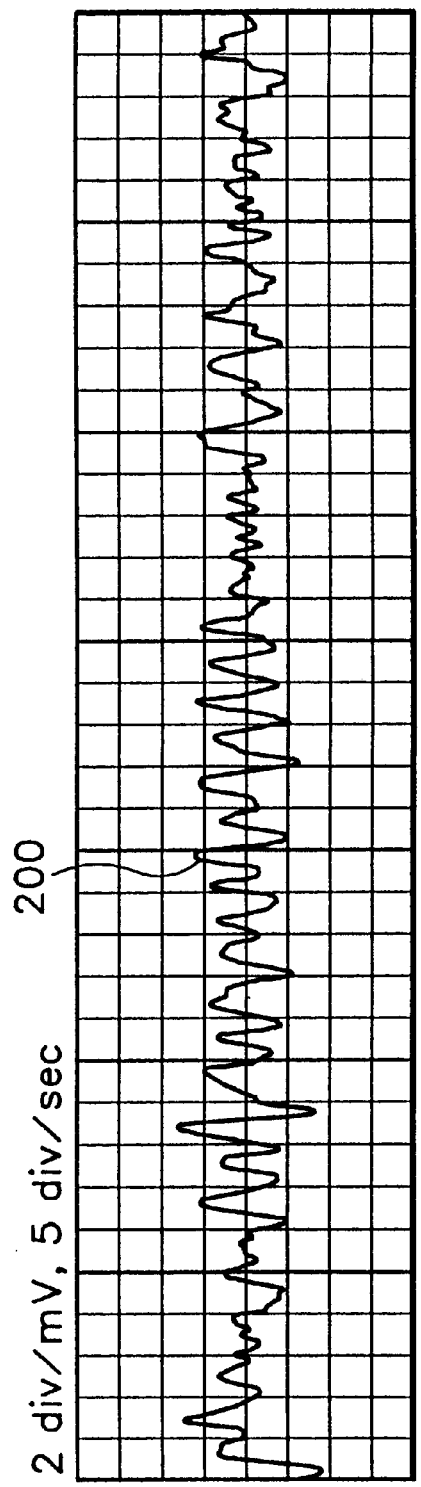
FIG. 3 shows an exemplary course VF waveform associated with a relatively healthy heart.
Figure 4:
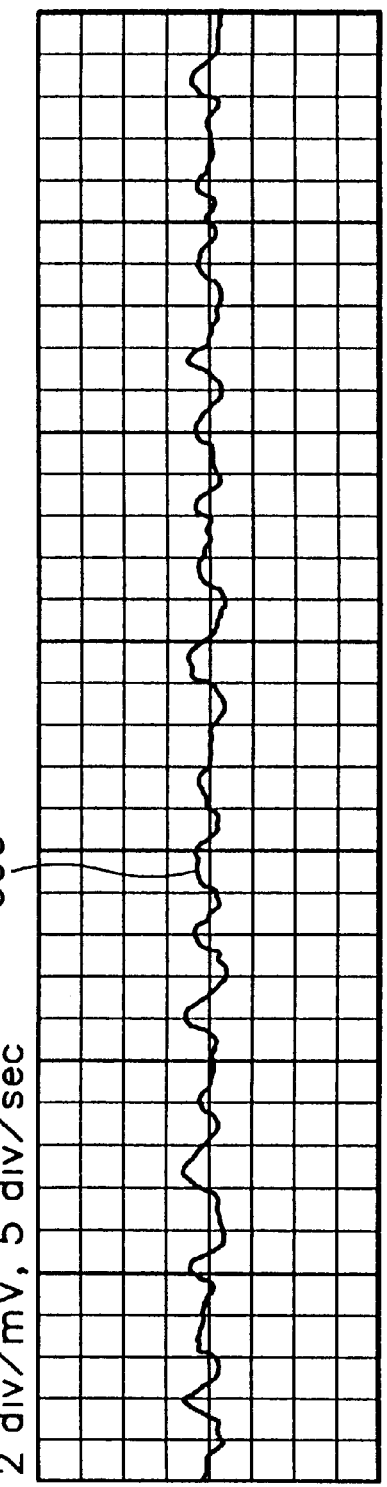
FIG. 4 shows an exemplary fine VF waveform associated with a highly ischemic heart.

The characteristic of an arrhythmia changes with increasing duration of the arrhythmia and the associated heart ischemia or relative healthiness of the heart. Arrhythmia is typically categorized as course arrhythmia or fine arrhythmia. Fine arrhythmia typically occurs in longer duration arrhythmia conditions. Course arrhythmia generally occurs during the earlier stages of arrhythmia. Therefore, course arrhythmia is also referred to as short duration arrhythmia, and fine arrhythmia is also referred to as long duration arrhythmia. The amplitude of the ECG waveform is one parameter that can be used to differentiate between course arrhythmia and long duration arrhythmia. ECG waveform amplitudes less than or equal to a predetermined value of amplitude, such as 200 mV, are typically classified as fine arrhythmia. ECG waveform amplitudes greater than the predetermined value of amplitude are classified as course arrhythmia. In general, during fine arrhythmia, as compared to course arrhythmia, the ECG waveform has lower overall amplitude, lower frequency components, and includes more a periodic components than course arrhythmia. Shown in FIG. 3 is an exemplary course arrhythmia waveform 200. Shown in FIG. 4 is an exemplary fine arrhythmia waveform 300.

The power spectrum of the ECG waveform provides another way, in addition to amplitude, to determine whether the arrhythmia is fine arrhythmia or course arrhythmia. Course arrhythmia is characterized by a power spectrum having most of the energy relatively narrowly concentrated around a primary frequency. Typically, this frequency is around 3 Hz. However, fine arrhythmia is characterized by a power spectrum having lower overall energy with this energy distributed more evenly over the spectrum and with the peaks having lower amplitude and greater width than in course arrhythmia. To determine whether the patient is in course arrhythmia or fine arrhythmia based upon the power spectrum of the ECG waveform, the median frequency of the power spectrum is determined and compared to a predetermined value of frequency, such as 3 HZ. If the median frequency of the ECG waveform is less than the predetermined value of frequency, this would indicate that the patient has entered fine arrhythmia.

The length of time that the patient has been experiencing fibrillation is another parameter that could be monitored in order to determine whether the patient is experiencing course arrhythmia or fine arrhythmia. The period of time for which the ECG waveform indicates that the patient's heart is in arrhythmia could be monitored by electrotherapy apparatus 30. After the expiration of a predetermined period of time, such as 60 seconds, for which the patient is determined to be in arrhythmia, the patient would be classified as experiencing fine arrhythmia. Prior to the expiration of the predetermined period of time, the patient would be classified as experiencing course arrhythmia.

It should be recognized that the transition between course arrhythmia and fine arrhythmia is generally not abrupt in time, but rather occurs over a time period. Therefore, it is conceivable that a variety of values of ECG waveform amplitude, ECG waveform median frequency, and arrhythmia duration could be used to indicate the presence of the fine arrhythmia or the course arrhythmia conditions. Furthermore, a combination of multiple parameters used to characterize the ECG waveform may be used to determine whether a patient is in course arrhythmia or fine arrhythmia. For example, the ECG waveform amplitude, the median frequency of the ECG power spectrum, and duration of fibrillation may all be determined. Then, then the values of two or three of these parameters could combined in order to determine if the patient is experiencing course arrhythmia or fine arrhythmia.

Course arrhythmia generally occurs during the early seconds of arrhythmia. Longer duration arrhythmia generally corresponds to fine arrhythmia. In general, the application of electrotherapy during fine arrhythmia is more likely to result in a systole and electro-mechanical dissociation. The application of electrotherapy during course arrhythmia is significantly less likely to result in a systole and electro-mechanical dissociation. Although arrhythmia has ceased during a systole and electro-mechanical dissociation, the heart is still not capable of pumping blood.

The differences in the ECG waveform between course arrhythmia and fine arrhythmia suggest that the underlying mechanism of fibrillation is different between these two conditions. During course arrhythmia, the potentials of the myocardial cells do not reach the resting potential because the myocardial cells are restimulated during the relative refractory period. However, during fine arrhythmia, the potentials of the myocardial cells may reach the resting potential before re-stimulation. Therefore, for fine arrhythmia and course arrhythmia the optimal electrotherapy to achieve defibrillation may be different. More specifically, myocardial cells during fine arrhythmia may actually be more easily stimulated. If this is the case, then the energy required for defibrillation of fine arrhythmia may be less than for course arrhythmia. Furthermore, applying excessive energy during defibrillation attempts may result in dysfunction and refibrillation of the heart. Additionally, it should be recognized that as well as changing the energy level of the electrotherapy applied between course arrhythmia and fine arrhythmia, the electrotherapy waveform that is optimal for course arrhythmia may not be optimal for fine arrhythmia. For example, with a bi-phasic electrotherapy waveform used to apply electrotherapy, the optimal duration of each of the phases may be different between course arrhythmia and fine arrhythmia.

As well as the possibility that the application of electrotherapy optimal for course arrhythmia is not optimal for fine arrhythmia, there is the possibility that excessive energy may be applied to the heart by applying electrotherapy optimal for course arrhythmia to a patient experiencing fine arrhythmia. During fine arrhythmia, the myocardial cells begin to suffer from a lack of oxygen. The condition of the myocardial cells during long arrhythmia may make them more susceptible to degradation resulting from the currents that flow in the myocardium during the defibrillation. Therefore, adjustment of the electrotherapy applied to the patient based upon the type of arrhythmia will, in addition to improving the likelihood of successful defibrillation, reduce the likelihood of applying excessive energy to the heart and causing dysfunction.

The electrotherapy apparatus 30 shown in FIG. 1 can be used to vary either or both, the duration of the electrotherapy waveform and the energy level of the electrotherapy waveform. For the embodiment of the electrotherapy apparatus shown in FIG. 2, varying the energy level of the electrotherapy waveform could be accomplished by adjusting the initial voltage to which capacitor 100 is charged.

Figure 5:
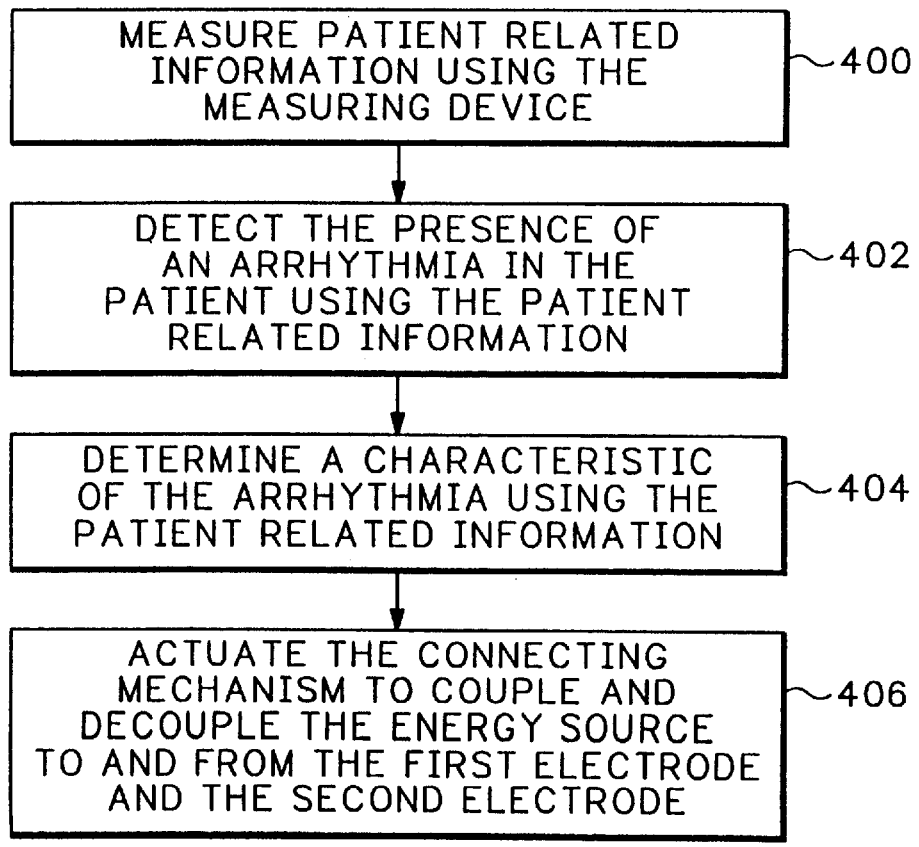
FIG. 5 shows a high level flow diagram of a method for using the electrotherapy apparatus shown in FIG. 1.

Shown in FIG. 5 is a high level flow diagram of a method for performing electrotherapy on a patient. The method shown in FIG. 5 could use the hardware shown in FIG. 1 to perform the electrotherapy. In a first act 400, measuring device 40 measures patient related information, which may include, for example, an ECG waveform, and supplies it to controller 38. Next, in act 402, using the patient related information from measuring device 40, controller 38 detects the presence of an arrhythmia in the patient. Then, in act 404, controller 38 determines a characteristic of the arrhythmia using the patient related information. The characteristic of the arrhythmia provides an indication of the healthiness of the patient's heart. Finally, in act 406, controller 38 actuates the connecting mechanism to couple and decouple the energy source 32 to and from, respectively, the first electrode and the second electrode, thereby supplying an electrotherapy waveform to the patient. In doing so, an electrotherapy waveform is delivered to the patient having a property based upon the characteristic of the arrhythmia. The property that could be adjusted based upon the characteristic of the arrhythmia may include either or both the energy level or duration of the electrotherapy waveform applied to the patient.

Energy source 32 could include a high voltage power supply that can charge a capacitor to an initial voltage. The initial voltage level to which the capacitor is charged is selected based upon an analysis of the patient related information (such as an ECG waveform indicating arrhythmia) measured by measuring device 40. The analysis could take into account the degree to which the patient is experiencing either fine arrhythmia or course arrhythmia based upon the characteristic of the arrhythmia. Where measuring device 40 provides an ECG waveform, the characteristic could include one or more of the ECG waveform amplitude, ECG waveform power spectrum, or the duration of the arrhythmia. For example, if the analysis of the ECG waveform indicates that the patient is experiencing fine arrhythmia, the initial voltage on the capacitor could be set at a lower voltage (corresponding to the reduced level of energy required for defibrillation) than for course arrhythmia. Adjusting the initial energy based upon whether the patient is experiencing fine arrhythmia or course arrhythmia increases the likelihood of defibrillation while reducing the likelihood of applying excessive energy to the heart.

Alternatively, the energy delivered to the patient could be adjusted by controlling the duration of the electrotherapy waveform applied to the patient. If the electrotherapy waveform includes a multi-phasic waveform, such as a biphasic electrotherapy waveform, controlling the duration could be accomplished by controlling the duration of one or both of the phases. In another alternative, both the initial voltage on the capacitor and the duration of the electrotherapy waveform could be adjusted to control the energy delivered to the patient based upon the characteristic of the arrhythmia.

Although several embodiments of the invention have been described, it is readily apparent to those of ordinary skill in the art that various modifications may be made without departing from the spirit of the invention or from the scope of the appended claims.

What is claimed is:

1. A defibrillator for delivering a multi-phasic waveform to a patient through a first electrode and a second electrode, the defibrillator comprising:

a capacitor having a first terminal and a second terminal, with the capacitor to store charge used for delivery of the multi-phasic waveform to the patient;

a power supply configured for charging the capacitor;

a connecting mechanism coupled between the first terminal and the second terminal of the capacitor and the first electrode and the second electrode to permit the first terminal of the capacitor to selectively couple to one of the first electrode and the second electrode and to permit the second terminal of the capacitor to selectively couple to one of the first electrode and the second electrode;

a waveform measuring device for measuring an ECG waveform; and a controller coupled to the connecting mechanism and arranged to receive the ECG waveform from the waveform measuring device, with the controller configured to adjust the multi-phasic waveform based upon the ECG waveform.

2. The defibrillator as recited in claim 1, wherein:

with the controller coupled to the power supply, the controller includes a configuration for configuring the power supply to set a voltage on the capacitor based upon the ECG waveform.

3. The defibrillator as recited in claim 2, wherein:

the controller includes a configuration to actuate the connecting mechanism to adjust a duration of the coupling of the capacitor to the first electrode and the second electrode based upon the ECG waveform.

4. The defibrillator as recited in claim 3, wherein:

the controller includes a configuration to detect a presence of either course arrhythmia or fine arrhythmia by comparing an amplitude of the ECG waveform to a predetermined value.

5. The defibrillator as recited in claim 4, wherein:

the arrhythmia includes ventricular fibrillation.

6. The defibrillator as recited in claim 3, wherein:

the controller includes a configuration to detect a presence of either course arrhythmia or fine arrhythmia by comparing a power spectrum of the ECG waveform to a predetermined power spectrum.

7. The defibrillator as recited in claim 6, wherein:

the arrhythmia includes ventricular fibrillation.

8. The defibrillator as recited in claim 3, wherein:

the multi-phasic waveform includes a bi-phasic waveform;

the controller includes a configuration to actuate the connecting mechanism to deliver the bi-phasic waveform to the patient through the first electrode and the second electrode; and the controller includes a configuration to set a duration of a first phase and a duration of a second phase of the bi-phasic waveform based upon detecting a presence of either course arrhythmia or fine arrhythmia.

9. The defibrillator as recited in claim 8, wherein:

the arrhythmia includes ventricular fibrillation.

* * * * *